United States Patent
Imai et al.

(10) Patent No.: US 6,740,219 B2
(45) Date of Patent: May 25, 2004

(54) ELECTROPHORESIS ANALYSIS APPARATUS AND SAMPLE VESSEL USED THEREFOR

(75) Inventors: Kazumichi Imai, Hitachinaka (JP); Osamu Uchida, Mito (JP)

(73) Assignees: Hitachi, Ltd., Tokyo (JP); Naka Instruments Co., Ltd., Hitachinaka (JP)

( * ) Notice: Subject to any disclaimer, the term of this patent is extended or adjusted under 35 U.S.C. 154(b) by 217 days.

(21) Appl. No.: 09/852,269

(22) Filed: May 10, 2001

(65) Prior Publication Data

US 2001/0027919 A1 Oct. 11, 2001

Related U.S. Application Data

(63) Continuation of application No. 09/132,323, filed on Aug. 11, 1998, now Pat. No. 6,325,908.

(30) Foreign Application Priority Data

Aug. 26, 1997 (JP) .............................................. 9-229080

(51) Int. Cl.⁷ ..................... G01N 27/447; G01N 27/453
(52) U.S. Cl. ....................................... 204/603; 204/604
(58) Field of Search ............................... 204/450, 451, 204/452, 453, 454, 455, 600, 601, 602, 603, 604, 605

(56) References Cited

U.S. PATENT DOCUMENTS

| | | | |
|---|---|---|---|
| 5,274,240 A | 12/1993 | Mathies et al. | 250/458 |
| 5,277,780 A | 1/1994 | Kambara | 204/299 |
| 5,366,608 A | 11/1994 | Kambara | 204/299 |
| 5,372,695 A | 12/1994 | Demorest | 204/603 |
| 5,384,024 A | 1/1995 | Moring et al. | 204/604 |
| 5,413,686 A | 5/1995 | Klein et al. | 204/603 |
| 5,439,578 A | 8/1995 | Dovichi et al. | 204/603 |
| 5,541,420 A | 7/1996 | Kambara | 204/602 |
| 5,585,069 A | 12/1996 | Zanzucchi et al. | 204/600 |
| 5,730,850 A | 3/1998 | Kambara et al. | 204/603 |
| 5,885,430 A * | 3/1999 | Kernan et al. | 204/453 |
| 5,916,428 A | 6/1999 | Kane et al. | 204/601 |

OTHER PUBLICATIONS

Jansson et al, Journal of Chromatography, 626, pp. 310–314, 1992.*

Jansson et al.: *Micro vials on a silicon wafer for sample introduction in capillary electrophoresis*, J. Chromatog., 626, pp. 310–314, 1992.

* cited by examiner

*Primary Examiner*—Kaj K. Olsen
(74) *Attorney, Agent, or Firm*—Kenyon & Kenyon (57) ABSTRACT

A multi-capillary type electrophoresis analysis apparatus has a sample tray for containing a plurality of samples, wherein part of the sample tray is made from a conductive material. Samples are introduced by applying a high voltage from a high voltage power supply between the sample tray and a coupler in a state in which one-ends of the capillaries are inserted in the samples contained in the sample tray. The apparatus eliminates the necessity of individually inserting electrodes in a plurality of samples contained in the sample tray, thereby making easy works for analysis.

14 Claims, 7 Drawing Sheets

ELECTROPHORESIS ANALYSIS APPARATUS AND SAMPLE VESSEL USED THEREFOR

This is a continuation of application Ser. No. 09/132,323, filed Aug. 11, 1998, now U.S. Pat. No. 6,325,908.

BACKGROUND OF THE INVENTION

The present invention relates to an electrophoresis analysis apparatus and a sample vessel used therefor, and particularly to an electrophoresis analysis apparatus suitably used for a DNA sequencer (DNA base sequence analyzer) for analyzing biochemical samples such as a DNA (Deoxyribonucleic acid) using a plurality of capillaries or micropassages as migration separation media, and a sample vessel used therefor.

A DNA analysis technology based on electrophoresis, particularly, a DNA sequencer (DNA base sequence analyzer) has been widely available. With the increased need for analysis, the necessity of improving the analysis throughput has been increased. One method of increasing the analysis throughput is to integrate electrophoresis media.

A thin gel layer formed between two flat glass plates has been conventionally used as electrophoresis separation media. On the other hand, a multi-capillary method using a plurality of capillaries each having a fine inside diameter has been proposed, for example, in Nature, Vol. 361 (1993), Kanbara, PP. 565–566, the specifications of U.S. Pat. Nos. 5,277,780, 5,366,608, and 5,274,240, Japanese Patent Laid-open No. Hei 5-72177, and PCT international publication for patent application No. Hei 7-503322. Such a method makes it possible to increase the degree of integration by making use of the fine inside diameters of the capillaries and to simultaneously analyze a large number of samples. In this method, further, since the cross section of migration passages becomes smaller than that of the conventional flat glass plates, a current caused by electrophoresis becomes smaller to thereby suppress generation of a Joule heat. As a result, by applying a higher electrophoresis voltage, a sample can be migrated at a higher speed. Accordingly, a number of samples can be simultaneously separated and analyzed at a high speed.

As a second method, a multi-capillary method of making use of fine grooves formed in a surface portion of a glass plate as migration passages has been proposed, for example, in the specification of U.S. Pat. No. 5,192,412 and Japanese Patent Laid-open No. Hei 5-93711. Even in this method, a number of samples can be simultaneously separated and analyzed at a high speed.

In the above-described multi-capillary method, first ends of an electrode and a capillary are first inserted in a sample contained in a sample vessel, followed by applying a voltage across the capillary to electrically migrate the sample into the capillary; and then the first ends of the electrode and the capillary are inserted in a buffer solution in a buffer bath, followed by applying a voltage across the capillary to separate the sample by electrophoresis.

In this case, where the number of samples to be simultaneously analyzed is several pieces, since the number of electrodes/capillaries is the same as that of the samples, it does not take as much labor to insert the electrodes and capillaries in sample vessels and a buffer bath.

However, in the case where several tens of samples are simultaneously analyzed to improve the analysis throughput, it is difficult to insert electrodes and capillaries in sample vessels and a buffer bath. To be more specific, the amount of a sample generally used for a DNA sequencer is merely 5 $\mu$l because it is difficult to prepare a large amount of a sample and also a reagent to be used is expensive. In the case where the sample in an amount of 5 $\mu$l is put in a sample vessel having an inner diameter of 2 mm, the liquid level becomes only about 1.5 mm. It is very difficult to individually insert several tens of electrodes and capillaries in the above small-sized sample vessels.

SUMMARY OF THE INVENTION

An object of the present invention is to provide a multi-capillary type electrophoresis analysis apparatus capable of simplifying analysis and a sample vessel used therefor.

According to the present invention, there is provided an electrophoresis analysis apparatus having a plurality of migration passages and a detector for optically detecting a plurality of sample components separated by electrophoresis, including: a sample vessel for containing a plurality of samples to be introduced in the migration passages, at least part of a portion, of the sample vessel, to be in contact with these samples being made of a conductive material; wherein the samples are introduced in the migration passages by applying a voltage to the migration passages via the conductive material forming part of the sample vessels. With this configuration, since part of the sample vessel can be used as an electrode and thereby insertion of electrodes in samples can be eliminated, it is possible to simplify analysis.

The sample vessel preferably includes a plate portion having a plurality of openings and a metal base portion fixed on a bottom portion of the plate portion.

DETAILED DESCRIPTION

Hereinafter, preferred embodiments in which the present invention is applied to an electrophoresis analysis apparatus and sample vessels used therefor will be described with reference to FIGS. 1 to 11.

Figure 1:
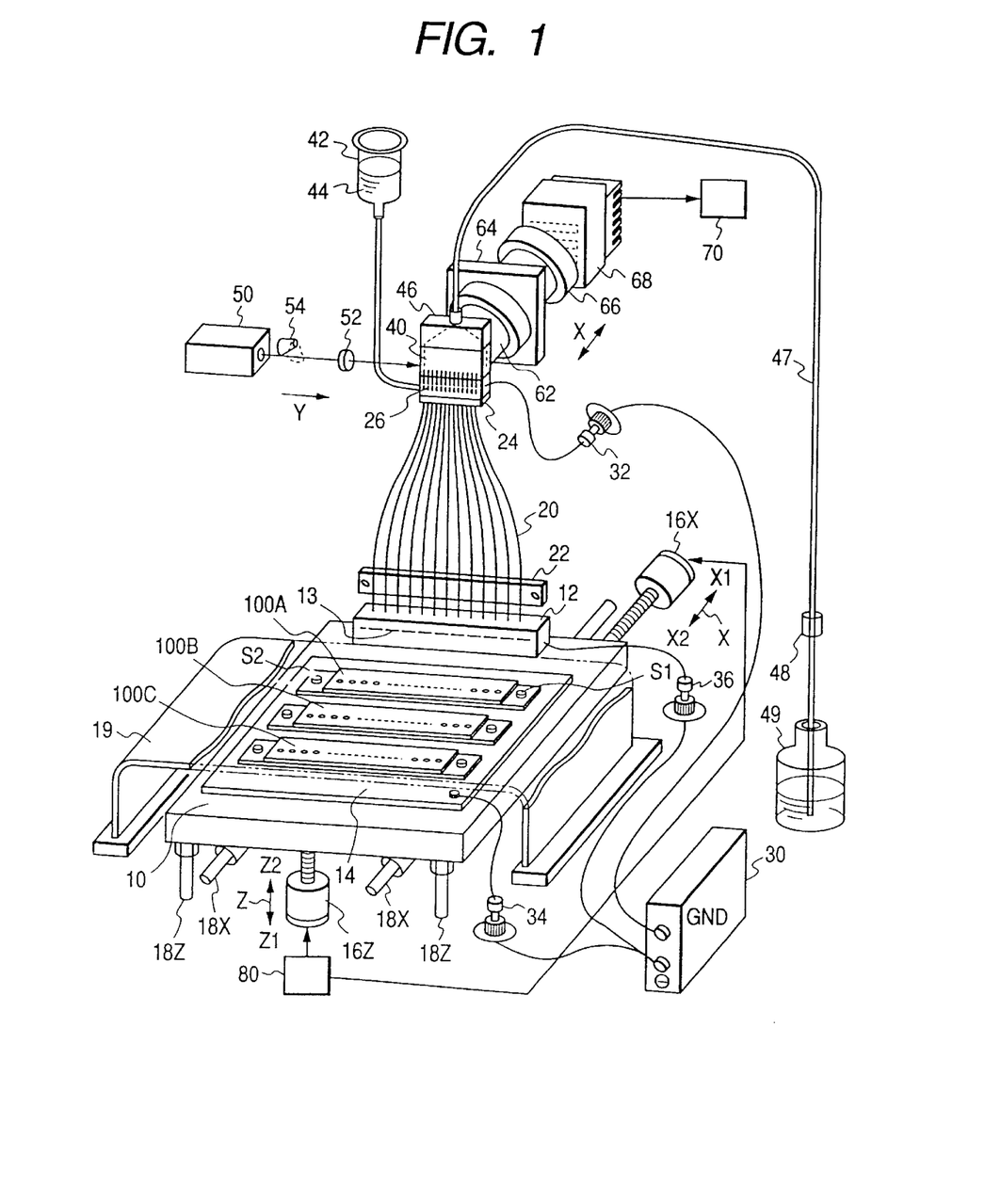
FIG. 1 is a perspective view showing the entire configuration of an electrophoresis analysis apparatus according to one embodiment of the present invention.

Referring first to FIG. 1, there will be described the entire configuration of the electrophoresis analysis apparatus according to one embodiment of the present invention.

FIG. 1 is a perspective view showing the entire configuration of the electrophoresis analysis apparatus according to an embodiment of the present invention.

First, the entire configuration will be described below.

A migration buffer bath 12 containing a buffer (electrolyte) is disposed on a moving mechanism 10. A platinum electrode 13 is stretchingly mounted in the migration buffer bath 12 in such a manner as to be in contact with the buffer. On the moving mechanism 10 are also disposed three sample trays 100A, 100B and 100C via a sample tray holder 14. As will be described later with reference to FIG. 2, the sample tray 100A includes 48 pieces of sample vessels. The sample tray 100A is removably fixed on the sample tray holder 14 with set screws S1 and S2. The bottom portion of the sample tray 100A is made of a conductive metal such as a stainless steel, and is electrically connected to the sample tray holder 14 which is made of a conductive metal such as a stainless steel. Similarly, each of the sample trays 100B and 100C includes 48 pieces of sample vessels and has a bottom portion which is electrically connected to the sample tray holder 14.

The moving mechanism 10 is vertically movable in the Z-axis direction along vertical slide guides 18Z using a vertically moving motor 16Z. The moving mechanism 10 is also longitudinally movable in the X-axis direction along longitudinal slide guides 18X using a longitudinally moving motor 16X. The motors 16Z and 16X are controlled by a controller 80. A transparent cover 19 made of polyvinyl chloride or polyacrylate or polymethacrylate resin is disposed in such a manner as to cover the three sample trays 100A, 100B and 100C for suppressing evaporation of samples held in the sample vessels and preventing contamination of the sample vessels with external dust.

The electrophoresis analysis apparatus includes 48 pieces of capillaries 20 disposed in parallel, each of which is filled with a gel matrix for separation. The lower end sides of the capillaries 20 are fixed by capillary retaining plate 22, and the lower ends of the capillaries 20 are inserted in the buffer in the migration buffer bath 12. The upper end sides of the capillaries 20 are fixed by a capillary retaining plate 24, and the upper ends of the capillaries 20 are fixedly connected to a coupler 26.

The coupler 26 is connected to an electrode plug 32 on the earth side, and the electrode plug 32 is in turn connected to an earth electrode of a high voltage power supply 30. The sample tray holder 14 is connected to an electrode plug 34 on the high voltage side, and the platinum electrode 13 in the buffer bath 12 is connected to an electrode plug 36 on the high voltage side. The electrode plugs 34 and 36 are connected to a high voltage (−) electrode of the high voltage power supply 30.

The coupler 26 is connected to a sheath flow cell 40, into which a sheath liquid 44 held in a sheath liquid tank 42 is introduced by the gravity. Samples, which are separated by migration in the capillaries 20 and flow out of migration terminals of the capillaries 20, are carried to the upper side with the sample components in the capillaries left as separated.

Laser light emitted from a laser 50 is collimated into parallel light beams by a lens 52, and the sheath flow cell 40 is irradiated with the laser beams from its side surface (in the Y-direction in the drawing), to excite the separated sample in the sheath flow cell 40. A shutter 54 is provided between the laser 50 and the lens 52 for selectively exciting the sample. Fluorescent light generated by laser irradiation is taken out along the X-axis direction perpendicular to the Y-axis direction, and converged through a condenser lens 62. Then, a light component having a specific wavelength to be detected is selected from the fluorescent light by a filter 64 and is focused through an image forming lens 66 at an optical sensor 68 such as a two-dimensional CCD sensor. A signal detected by the optical sensor 68 is fed to a signal processor 70, being processed to identify the kind of the terminal base on the basis of the wavelength of the fluorescent light, and the base sequence of the nucleic acid sample is analyzed on the basis of the measured signal.

In determination of the base sequence of a DNA (Deoxyribonucleic Acid), measurement is generally performed for four kinds of wavelengths. Fluorescent dyes are previously combined in the reaction operation so that each maximum wavelength corresponds to the kind of a terminal base of a DNA fragment.

A drain adaptor 46 is mounted on the upper end of the sheath flow cell 40. The sample, which has flowed from the capillary 20 into the sheath flow cell 40, is discharged as a wastage into a drain bottle 49 through a drain tube 47. In the course of the drain tube 47 is provided a flow controller composed of an orifice and a plurality of capillaries for controlling the flow rate of the sample by making constant the passage resistance of the drain tube 47.

The entire operation of the electrophoresis analysis apparatus in this embodiment will be described below.

Samples to be analyzed are previously poured in specific amounts into 48 pieces of the sample vessels of each of the sample trays 100A, 100B and 100C. The sample trays 100A, 100B and 100C in which the samples are contained are fixed on the sample tray holder 14 with the set screws S1 and S2. The controller 80 drives the vertically moving motor 16Z to move down the moving mechanism 10 in the Z1 direction. The downward movement of the moving mechanism 10 is stopped at a position where the lower ends of the capillaries 20 are sufficiently separated from the buffer bath 12. Then, the controller 80 drives the longitudinally moving motor 16X to move the moving mechanism 10 in the X1 direction. The movement of the moving mechanism 10 is stopped at a position where the sample tray 100A is located directly under the capillaries 20. The controller 80 also drives the vertically moving motor 16Z to move up the moving mechanism 10 in the Z2 direction. The upward movement of the moving mechanism 10 is stopped at a position where the leading ends of the capillaries 20 are to be inserted in the samples in the sample vessels of the sample tray 100A. The positioning in the vertical movement and the longitudinal movement of the moving mechanism 10 is performed by a position detecting mechanism such as a switch provided in the moving mechanism 10.

By applying a high voltage from the high voltage power supply 30 between the sample tray 100A and the coupler 26 in a state in which the lower ends of the capillaries 20 are inserted in the samples, the samples in the sample vessels are introduced into the capillaries 20.

The controller 80 drives the vertically moving motor 16Z to move down the moving mechanism 10 in the Z1 direction. The downward movement of the moving mechanism 10 is stopped at a position where the lower ends of the capillaries 20 are sufficiently separated from the sample trays 100A. Then, the controller 80 drives the longitudinally moving motor 16X to move the moving mechanism 10 in the X2 direction. The movement of the moving mechanism 10 is stopped at a position where the buffer bath 12 is located directly under the capillaries 20. The controller 80 also drives the vertically moving motor 16Z to move up the moving mechanism 10 in the Z2 direction. The upward movement of the moving mechanism 10 is stopped at a position where the leading ends of the capillaries 20 are inserted in the buffer in the buffer bath 12. The positioning in the vertical movement and the longitudinal movement of the moving mechanism 10 is performed using a position detecting mechanism such as a switch provided in the moving mechanism 10.

By applying a high voltage from the high voltage power supply 30 between the platinum electrode 13 and the coupler 26 in a state in which the lower ends of the capillaries 20 are inserted in the buffer, the samples introduced in the capillaries 20 are separated by electrophoresis.

After the analysis of the samples in the sample tray 100A is completed, the samples in the sample trays 100B and 100C are introduced in the capillaries 20 in the same procedure as described above, to be thus separated by electrophoresis.

It takes about two hours to analyze one sample, and therefore, by provision of the three sample trays 100A, 100B and 100C on the sample tray holder 14 as shown in FIG. 1, it becomes possible to carry out automatic analysis for about six hours. The number of the sample trays is not limited to three pieces but may be four pieces or more.

The method of optically detecting the sample separated by electrophoresis is not limited to fluorescent light detection but may be absorbance detection.

The configuration of a sample vessel used in the electrophoresis analysis apparatus of the present invention will be described with reference to FIGS. 2 and 3.

Figure 2:
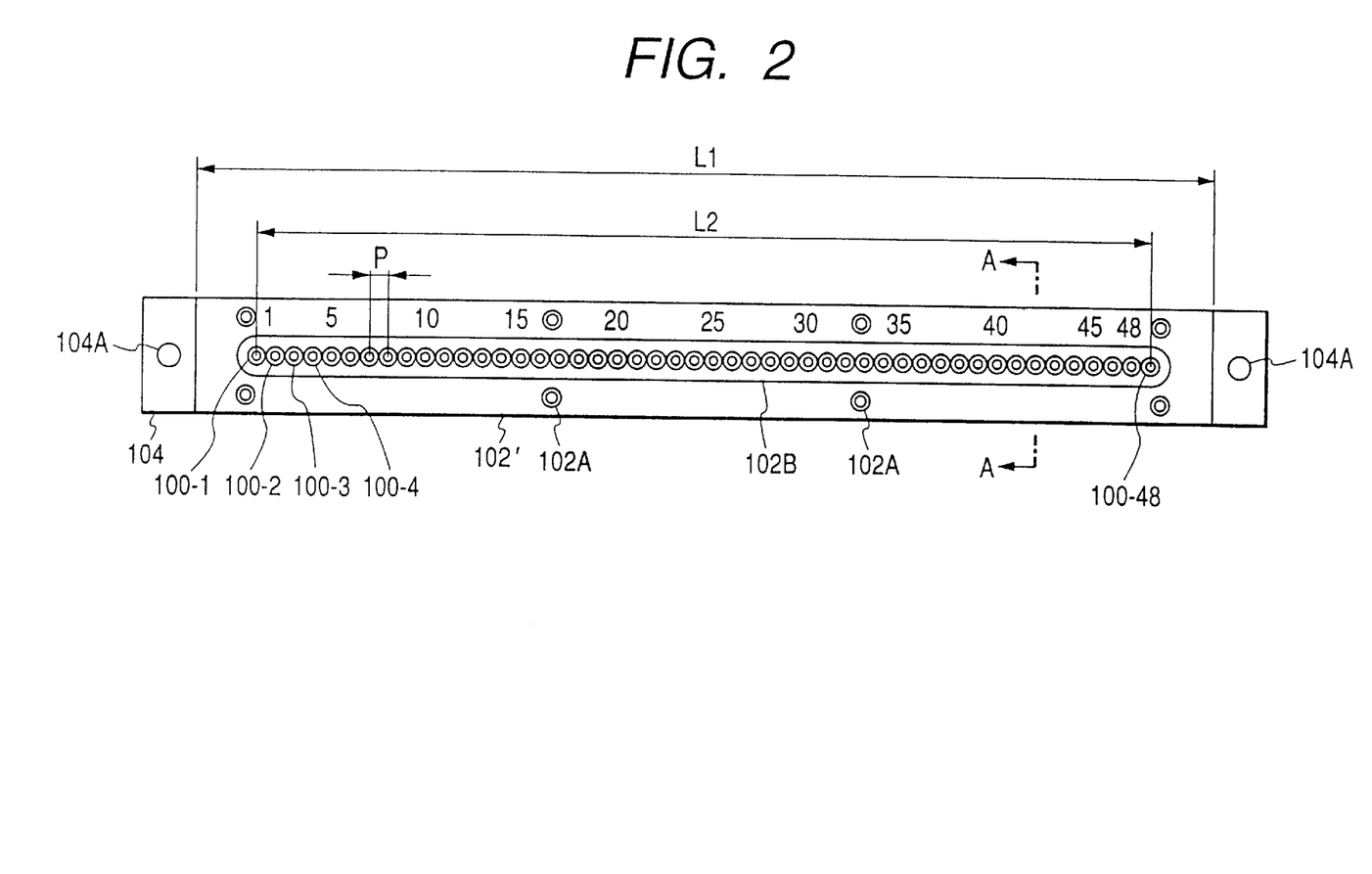
FIG. 2 is a plan view of sample vessels used for the electrophoresis analysis apparatus according to one embodiment of the present invention.
Figure 3:
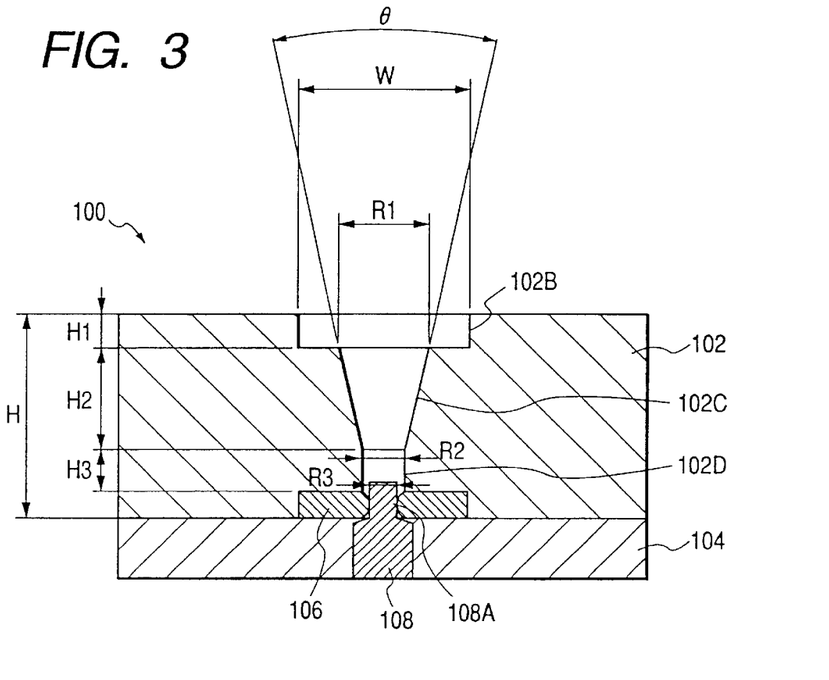
FIG. 3 is a sectional view taken on line A—A of FIG. 2.

FIG. 2 is a plan view of sample vessels used for the electrophoresis analysis apparatus according to one embodiment of the present invention, and FIG. 3 is a sectional view taken on line A—A of FIG. 2.

A sample tray 100 is formed into a rectangular shape in a plan view, in which 48 pieces of circular sample vessels 100-1, 100-2, ..., 100-48 are aligned. The sample tray 100 includes an upper sample plate 102 and a metal base 104 fixed on the backface of the sample plate 102. The sample plate 102 is made from a transparent polyacrylate or polymethacrylate resin, and has 48 pieces of circular openings for forming the sample vessels 100-1, 100-2, ..., 100-48. The sample plate 102 may be made from a transparent plastic material such as polyvinyl chloride or polycarbonate. Since the sample plate 102 is made from a transparent material, it is possible to easily, visually confirm samples contained in the sample vessels 100-1, 100-2, ..., 100-48 and the states of the capillaries inserted in the samples.

The sample plate 102 is fixed on the metal base 104 with eight screws. The metal base 104 is made of a stainless steel as a conductive material. The metal base 104 forms part of wall surfaces of the sample vessels 100-1, 100-2, ..., 100-48, and is used as an electrode common to samples contained in the sample vessels 100-1, 100-2, ..., 100-48. Since the metal base 104 forms part of the sample vessels, it is possible to eliminate the necessity of inserting electrodes in the samples as in the conventional apparatus. It is experimentally confirmed that the metal base 104 made of stainless steel, which is a widely available material, exhibits a sufficient durability. The electrophoresis analysis apparatus using the metal base 104 made of stainless steel is allowed to be continuously used for a period of six months or more only by periodically washing the sample tray 100. The conventional electrophoresis analysis apparatus is expensive because of use of a noble metal, such as platinum, as an electrode material; however, in the electrophoresis analysis apparatus of the present invention, the use of a stainless steel as an electrode material advantageously reduces the cost of the sample vessels.

Both end portions of the metal base 104 have circular holes 104A, and as described with reference to FIG. 1, the sample tray 100 is fixed on the metal sample tray holder with the set screws passing through the circular holes 104A.

The means for fixing the sample tray 100 on the sample tray holder is not limited to the set screws but may be plate springs or the like.

In place of the metal base 104, there may be used an insulating substrate on which a metal foil is stuck or a metal film is formed by vapor-deposition or sputtering. At this time, the metal foil or metal film forms part of the wall surfaces of the sample vessels, and it functions as a common electrode when it is made electrically conductive to the samples contained in the sample vessels.

As will be described later, a packing is inserted between the sample plate 102 and the metal base 104 for preventing leakage of samples in the sample vessels.

A length L1 of the sample plate 102 is set at 160 mm. A distance L2 from the center of the sample vessel 100-1 formed in the sample plate 102 to the center of the sample vessel 100-48 formed in the sample plate 102 is set at 141 mm. That is to say, a pitch P between the adjacent sample vessels is set at 3 mm. While the cross-sectional shape of the sample vessel will be described with reference to FIG. 3, an opening diameter of the uppermost portion of the sample vessel is set at φ 2.8 mm.

The pitch P between the adjacent sample vessels is set at a value obtained by dividing a pitch (9 mm) between adjacent holes formed in a microtiter plate by an integer number. The microtiter plate is generally used for preparation of samples. The pitch between adjacent pipets used for pipetting samples from the microtiter plate is equal to the pitch between the adjacent holes of the microtiter plate. If the pitch P between the adjacent sample vessels is, as described above, set at the value obtained by dividing the pitch (9 mm) between the adjacent holes of the microtiter plate by an integer number (for example 3 as shown in FIG. 2), that is, if the pitch P between the adjacent sample vessels is set at 3 mm, the samples can be pipetted from the microtiter plate into the sample vessels using the existing pipets. To be more specific, at the first pipetting, samples are poured in every fourth sample vessel, that is, in the order of the sample vessels 100-1, 100-4, ..., 100-46. At the second pipetting, after the pipets are shifted only 3 mm, samples are poured in every fourth sample vessel, that is, in the order of the sample vessels 100-2, 100-5, ..., 100-47. At the third pipetting, after the pipets are shifted only 3 mm, samples are poured in every fourth sample vessel, that is, in the order of the sample vessels 100-3, 100-6, ..., 100-48. In this way, while the pipetting of the samples is divided into three times, the samples can be poured in the sample vessels using the existing pipets.

The pitch P between the adjacent sample vessels, which is set at the value obtained by dividing the pitch (9 mm) between the adjacent holes of the microtiter plate, may be generally in a range of ½ to ¼ of the pitch (9 mm) between the adjacent holes of the microtiter plate in consideration of the poured amount of the sample and the dimension of the sample vessel.

The cross-sectional structure of the sample tray 100 will be described with reference to FIG. 3 which is an enlarged sectional view taken on line A—A of FIG. 2.

The sample plate 102 is fixed on the metal base 104 with the set screws as described with reference to FIG. 2. A groove is formed in the lower surface portion of the sample plate 102, and a packing 106 is previously inserted in the groove for preventing leakage of liquid from a space between the sample plate 102 and the metal base 104. The packing 106 is made from silicon rubber.

The cross-section of the sample plate 102 has a stepped portion 102B, a taper portion 102C, and a cylindrical portion 102D. The stepped portion 102B is formed into an elliptic shape as shown in FIG. 2, and it has a width W of 6 mm. When a height H of the sample plate 102 is 7 mm, a height H1 of the stepped portion 102B is 1.5 mm.

The taper portion 102C is formed into a cone shape having a taper angle θ of 24.4°. An opening diameter R1 of the taper portion 102C on the upper end side is φ 2.8 mm, and an opening diameter R2 of the taper portion 102C on the lower end side is φ 1.2 mm. The taper portion 102C allows easy insertion of a pipet or capillary in the sample vessel, and specifically, the taper portion 102C allows the leading end of the pipet or capillary to be easily bottomed. A height H2 of the taper portion 102C is set at 3.7 mm.

The cylindrical portion 102D has an opening diameter R2 of φ 1.2 mm and a height H3 of 1 mm. Assuming that the poured amount of a sample is 5 μl, the sample is contained substantially in the cylindrical portion 102D.

On the other hand, each metal pin 108 is previously press-fitted in the metal base 104. The number of the metal pins 108 is the same as that of the sample vessels, that is, 48 pieces in this embodiment. The metal pin 108 is made of the same material as that of the metal base 104, that is, a stainless steel. The leading end of the metal pin 108 has a projecting portion 108A having a diameter R3 of φ 0.8 mm. In a state in which the sample plate 102 is fixed on the metal base 104, the projecting portion 108A of the metal pin 108 slightly projects into the cylindrical portion 102D of the sample plate 102. With this configuration, the sample is certainly brought in electric-contact with the metal pin 108 and the metal base 104 used as an electrode.

In general, bubbles caused when a sample is poured in the sample vessel using a pipet possibly adhere on a wall surface of the sample vessel. If the bubbles adhere on the lowermost portion of the sample vessel and the capillary is inserted in the bubbles, the sample cannot be introduced into the capillary. To cope with such an inconvenience, the projecting portion 108A is provided in such a manner as to project into the cylindrical portion 102D. In this case, even if bubbles adhere on the bottom of the sample vessel, since the capillary is only inserted to the leading end of the projecting portion 108A, the sample can be introduced into the capillary by reducing the effect of the bubbles.

The opening diameter R1 of the upper end of the taper portion 102C which forms part of the sample vessel is set at φ 7 mm or less depending on the poured amount of a sample. In particular, if the poured amount of a sample is small, the opening diameter R1 is set at φ 3 mm or less, for example, φ 2.8 mm as described above. If the poured amount of a sample is smaller than that described above, the opening diameter R1 may be set at φ 2 mm or less.

As described above, while the sample tray 100 has a large number (48 pieces) of the sample vessels, since the conductive metal base and metal pins form part of the sample vessels and are taken as a common electrode, the necessity of inserting electrodes in the sample vessels as in the conventional apparatus can be eliminated. As a result, since only the capillaries may be inserted in the sample vessels, the preparation for analysis can be facilitated.

As described with reference to FIG. 1, since 48 pieces of the capillaries arranged in parallel are fixed in position by the capillary retaining plate 22, the capillaries of the multi-capillary type can be easily inserted in the sample vessels only by moving the sample tray 100 upward using the moving mechanism 10. As a result, the electrophoresis analysis can be automated using the electrophoresis analysis apparatus having the configuration shown in FIG. 1.

The configuration of a second sample vessel used for the electrophoresis analysis apparatus of the present invention will be described with reference to FIG. 4.

Figure 4:
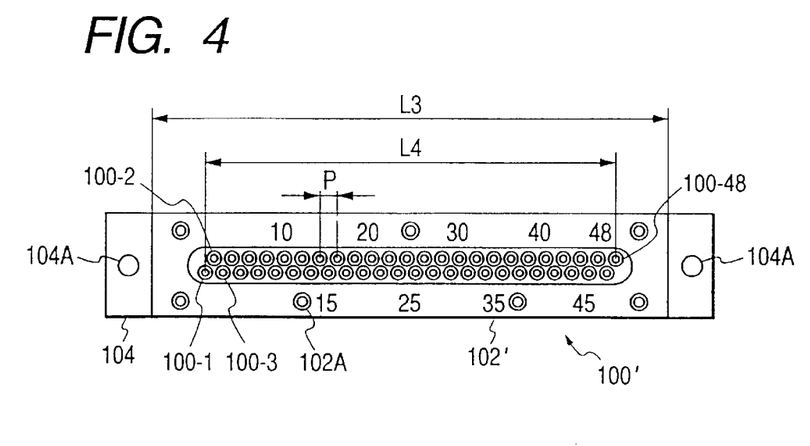
FIG. 4 is a plan view of second sample vessels used for the electrophoresis analysis apparatus according to one embodiment of the present invention.

FIG. 4 is a plan view of the second sample vessels used for the electrophoresis analysis apparatus according to one embodiment of the present invention.

A sample tray 100' in this embodiment is different from the sample tray 100 shown in FIG. 2 in that sample vessels 100-1, 100-2, . . . , 100-48 are arranged in a staggered pattern. The cross-sectional shape of the sample vessel is the same as described with reference to FIG. 3.

The sample tray 100' has a rectangular shape in a plan view, in which 48 pieces of the circular sample vessels 100-1, 100-2, . . . , 100-48 are arranged in a staggered pattern. The sample tray 100' has an upper sample plate 102' and a metal base 104 fixed on the backface of the sample plate 102'. The sample plate 102' is made from a transparent acrylic resin, and has 48 pieces of circular openings for forming the sample vessels 100-1, 100-2, . . . , 100-48.

The sample plate 102' is fixed on the metal base 104 with eight screws. The metal base 104 is made of a stainless steel as a conductive material. The metal base 104 forms part of wall surfaces of the sample vessels 100-1, 100-2, . . . , 100-48, and is used as an electrode common to samples contained in the sample vessels 100-1, 100-2, . . . , 100-48. Since the metal base forms part of the sample vessels, it is possible to eliminate the necessity of inserting electrode in samples as in the conventional apparatus.

Both end portions of the metal base 104 have circular holes 104A. As described with reference to FIG. 1, the sample tray 100' is fixed on a metal made sample tray holder with set screws.

As described with reference to FIG. 3, a packing is inserted between the sample plate 102' and the metal base 104 for preventing leakage of samples in the sample vessels.

A length L3 of the sample plate 102' is set at 128 mm. A distance L4 from the center of the sample vessel 100-1 formed in the sample plate 102' to the center of the sample vessel 100-48 formed in the sample plate 102' is set at 106 mm. A pitch P between the adjacent sample vessels is set at 3 mm.

By arranging the sample vessels in the sample tray 100' in the staggered pattern, the length of the sample tray 100' can be shortened, to thereby miniaturize the electrophoresis analysis apparatus, particularly, the moving mechanism.

The configuration of a third sample vessel used for the electrophoresis analysis apparatus of the present invention will be described with reference to FIG. 5.

Figure 5:
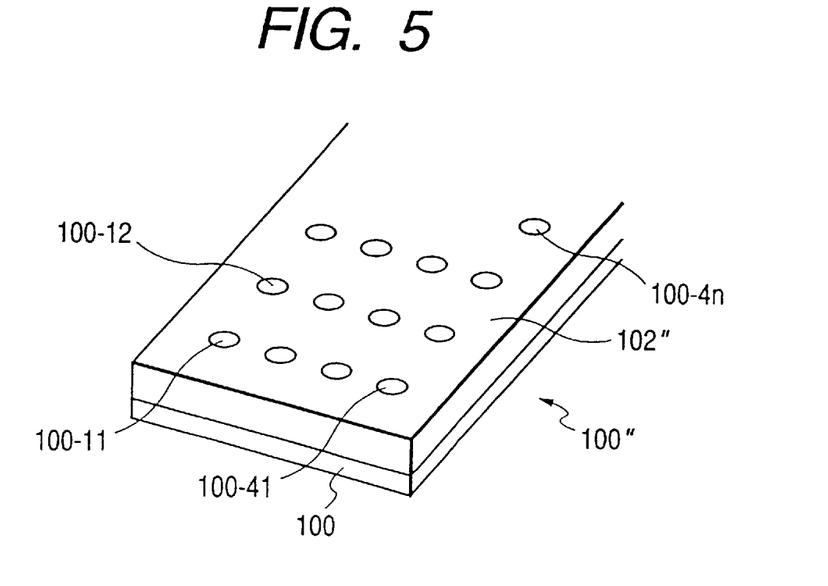
FIG. 5 is a perspective view of third sample vessels used for the electrophoresis analysis apparatus according to one embodiment of the present invention.

FIG. 5 is a perspective view of the third sample vessels used for the electrophoresis analysis apparatus according to one embodiment of the present invention.

A sample tray 100" in this embodiment is different from the sample tray 100 or 100' shown in FIG. 2 or 4 in that 4n pieces of sample vessels 100-11, 100-12, . . . , 100-21, . . . , 100-31, . . . , 100-41, . . . , 100-4n are arranged in four rows. The cross-sectional shape of the sample vessel is the same as described with reference to FIG. 3.

The sample tray 100" has a rectangular shape in a plan view, in which 4n pieces of the circular sample vessels 100-11, 100-12, . . . , 100-21, . . . , 100-31, . . . , 100-41, . . . , 100-4n are arranged in a matrix pattern of four rows (n pieces for each row). The sample tray 100" has an upper sample plate 102" and a metal base 104 fixed on the backface of the sample plate 102". The sample plate 102" is made from a transparent acrylic resin, and has 4n pieces of circular openings for forming the sample vessels 100-11, . . . , 100-4n.

The sample plate 102" is fixed on the metal base 104 with screws. The metal base 104 is made of a stainless steel as a conductive material. The metal base 104 forms part of wall surfaces of the sample vessels 100-11, . . . , 100-4n, and is used as an electrode common to samples contained in the sample vessels 100-11, . . . , 100-4n. Since the metal base forms part of the sample vessels, it is possible to eliminate the necessity of inserting electrodes in samples as in the conventional apparatus.

The sample tray 100" is fixed on a metal sample tray holder with set screws. As described with reference to FIG. 3, a packing is inserted between the sample plate 102" and the metal base 104 for preventing leakage of samples in the sample vessels. A pitch P between the adjacent sample vessels is set at a value obtained by dividing a pitch (9 mm) between adjacent holes of the microtiter plate by an integer number.

By arranging a plurality of rows of the sample vessels in the sample tray 100", the length of the sample tray 100" can be shortened, to thereby miniaturize the electrophoresis analysis apparatus, particularly, the moving mechanism.

The cross-sectional structure of a fourth sample vessel used for the electrophoresis analysis apparatus of the present invention will be described with reference to FIG. 6.

Figure 6:
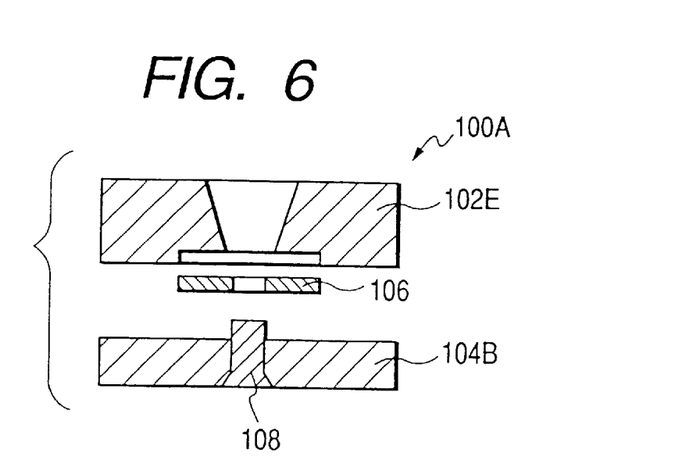
FIG. 6 is a sectional view of a fourth sample vessel used for the electrophoresis analysis apparatus according to one embodiment of the present invention.

FIG. 6 is a sectional view of the fourth sample vessel used for the electrophoresis analysis apparatus according to one embodiment of the present invention. In addition, the planar shape of a sample tray in which a plurality of the sample vessels are arranged is the same as that shown in FIG. 2, 4 or 5.

A sample tray 100A in this embodiment includes a sample plate 102E composed of a transparent plate made of an acrylic resin, an insulating base 104B, a packing 106 made of silicon rubber, and metal pins 108 made of a conductive material such as a stainless steel. The sample plate 102E has a taper portion functioning as a sample vessel. That is to say, a sample is contained in the taper portion of the sample plate 102E. The metal pin 108 is brought in electric-contact with a sample and functions as an electrode. Since a plurality of the sample vessels are formed in the sample tray 100A, the metal pins 108 of the same number as that of the sample vessels are provided in such a manner as to be electrically connected to the metal sample tray holder shown in FIG. 1.

The sample plate 102E is fixed on a base 104B with screws. A groove is formed in a lower surface portion of the sample plate 102E, and a packing 106 is previously inserted in the groove for preventing leakage of liquid from a space between the sample plate 102E and the base 104B.

By independently connecting a plurality of the metal pins 108 to a high voltage power supply and also connecting a current detection circuit between each metal pin and the high voltage power supply, it is possible to monitor a current for each sample.

The cross-sectional structure of a fifth sample vessel used for the electrophoresis analysis apparatus of the present invention will be described with reference to FIG. 7.

Figure 7:
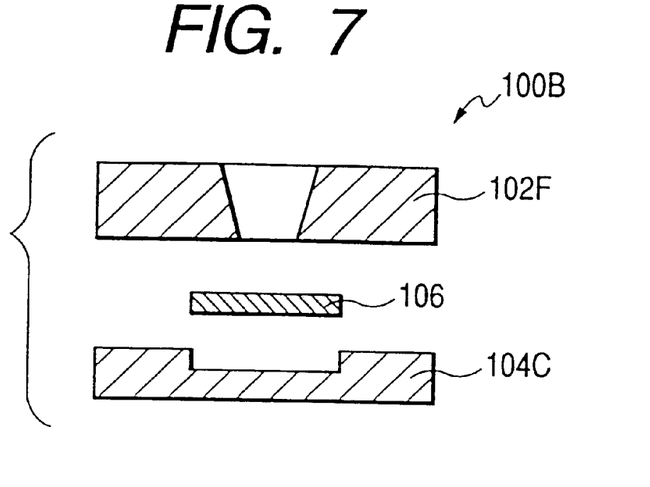
FIG. 7 is a sectional view of a fifth sample vessel used for the electrophoresis analysis apparatus according to one embodiment of the present invention.

FIG. 7 is a sectional view of the fifth sample vessel used for the electrophoresis analysis apparatus according to one embodiment of the present invention. In addition, the planar shape of a sample tray in which a plurality of the sample vessels are arranged is the same as that shown in FIG. 2, 4 or 5.

A sample tray 100B in this embodiment includes a metal sample plate 102F, an insulating base 104C, and a packing 106 made of silicon rubber. The sample plate 102F is formed with a taper portion functioning as a sample vessel. That is to say, a sample is contained in the taper portion of the sample plate 102F. Further, the sample plate 102F made of a conductive material has a function as an electrode.

The sample plate 102F is fixed on the base 104C with screws. A groove is formed in an upper surface portion of the base 104C, and a packing 106 is previously inserted in the groove for preventing leakage of liquid from a space between the sample plate 102F and the base 104C.

The cross-sectional structure of a sixth sample vessel used for the electrophoresis analysis apparatus of the present invention will be described with reference to FIG. 8.

Figure 8:
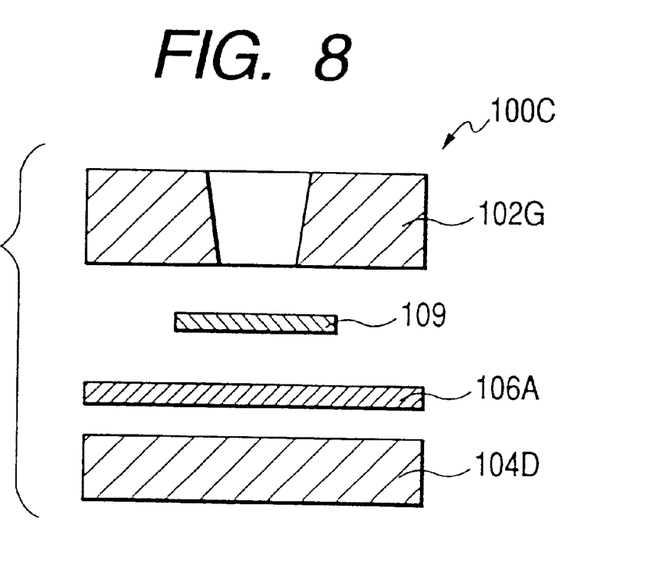
FIG. 8 is a sectional view of a sixth sample vessel used for the electrophoresis analysis apparatus according to one embodiment of the present invention.

FIG. 8 is a sectional view of the sixth sample vessel used for the electrophoresis analysis apparatus according to one embodiment of the present invention. In addition, the planar shape of a sample tray in which a plurality of the sample vessels are arranged is the same as that shown in FIG. 2, 4 or 5.

A sample tray 100C in this embodiment includes an insulating sample plate 102G, an insulating base 104D, a packing 106A made from silicon rubber, and a metal seat 109. The sample plate 102G has a taper portion functioning as a sample vessel. That is to say, a sample is contained in the taper portion of the sample plate 102G.

The sample plate 102G is fixed on the base 104D with screws. The metal seat 109 and the packing 106A made from silicon rubber are held between the sample plate 102G and the base 104D. The metal seat 109 is brought in contact with a sample and functions as an electrode. The packing 106A prevents leakage of liquid from a space between the sample plate 102G and the base 104D.

The cross-sectional structure of a seventh sample vessel used for the electrophoresis analysis apparatus of the present invention will be described with reference to FIG. 9.

Figure 9:
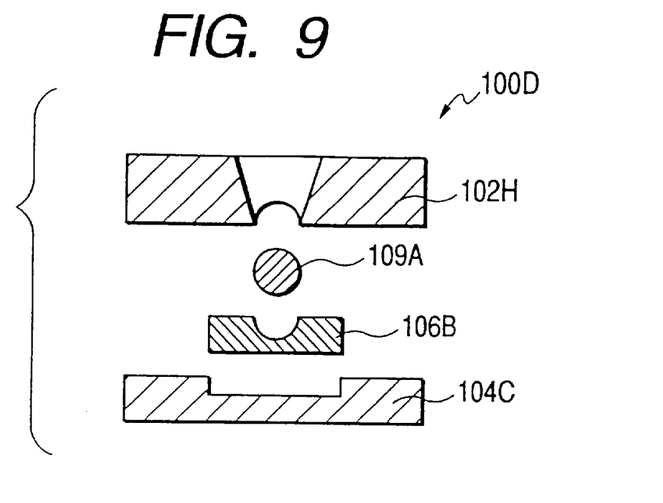
FIG. 9 is a sectional view of a seventh sample vessel used for the electrophoresis analysis apparatus according to one embodiment of the present invention.

FIG. 9 is a sectional view of the seventh sample vessel used for the electrophoresis analysis apparatus according to one embodiment of the present invention. In addition, the planar shape of a sample tray in which a plurality of the sample vessels are arranged is the same as that shown in FIG. 2, 4 or 5.

A sample tray 100D in this embodiment includes an insulating sample plate 102H, an insulating base 104C, a packing 106B made from silicon rubber, and a metal wire 109A. The sample plate 102H has a taper portion functioning as a sample vessel. That is to say, a sample is contained in the taper portion of the sample plate 102H.

The sample plate 102H is fixed on the base 104C with screws. The metal wire 109A and the packing 106B made from silicon rubber are held between the sample plate 102H and the base 104C. The metal wire 109A is brought in contact with a sample and functions as an electrode. The packing 106B prevents leakage of liquid from a space between the sample plate 102H and the base 104C.

The structure of an electrode portion of an eighth sample vessel used for the electrophoresis analysis apparatus of the present invention will be described with reference to FIG. 10.

Figure 10:
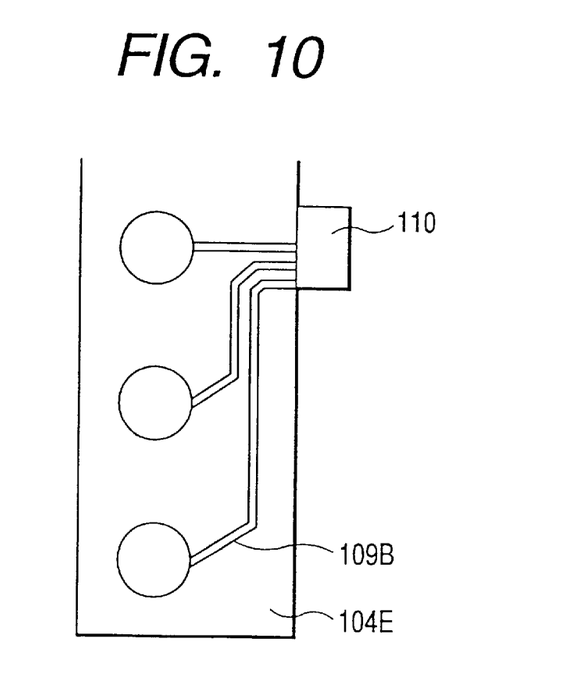
FIG. 10 is a plan view of an electrode portion of eighth sample vessels used for the electrophoresis analysis apparatus according to one embodiment of the present invention.

FIG. 10 is a plan view of an electrode portion of the eighth sample vessel used for the electrophoresis analysis apparatus according to one embodiment of the present invention. In addition, the planar shape of a sample tray in which a plurality of the sample vessels are arranged is the same as that shown in FIG. 2, 4 or 5. The cross-sectional structure is also the same as that shown in, for example, in FIG. 8.

In this embodiment, a metal film is formed on an insulating base 104C by vapor-deposition, and electrode patterns 109B are formed by selective etching. The electrode patterns 109B are connected to a high voltage power supply via a connector 110.

The structure of a ninth sample vessel used for the electrophoresis analysis apparatus of the present invention will be described with reference to FIG. 11.

Figure 11:
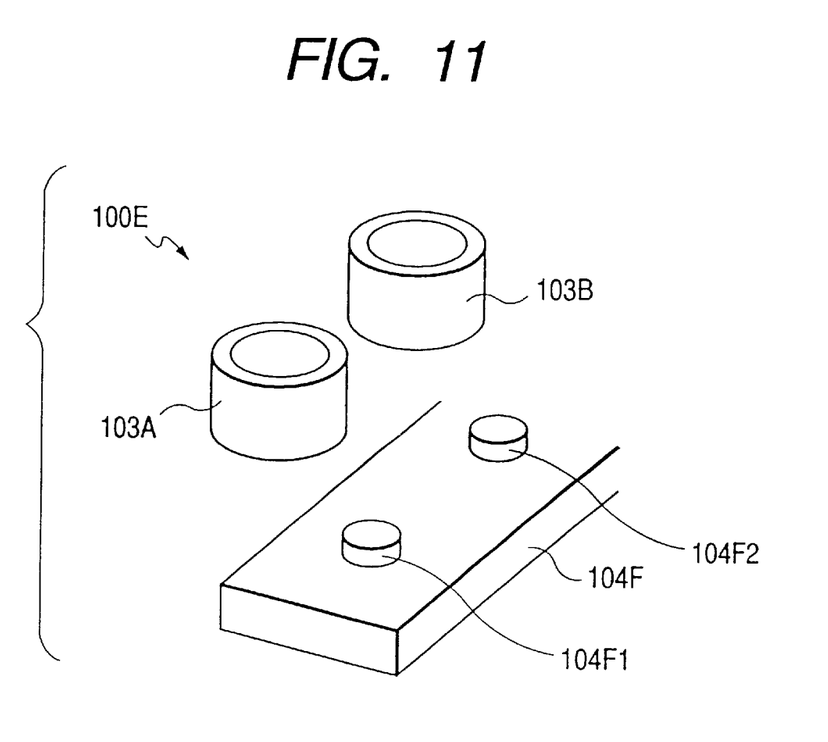
FIG. 11 is a perspective view of an electrode portion of ninth sample vessels used for the electrophoresis analysis apparatus according to one embodiment of the present invention.

FIG. 11 is a plan view of an electrode portion of the ninth sample vessel used for the electrophoresis analysis apparatus according to one embodiment of the present invention.

In this embodiment, metal made projections 104F1 and 104F2 are integrally formed on a base 104F made of a metal such as a stainless steel. Insulating rings 103A and 103B are inserted around the projections 104F1 and 104F2, respectively, to form sample vessels.

The base 104F functions as an electrode for each sample vessel.

As the conductive material forming part of the sample vessel, a conductive rubber or conductive organic material may be used in place of a metal.

In the above description, part of the sample tray is made of a conductive material; however, the entire sample tray may be made of metal.

As described above, according to this embodiment, since part of the plurality of the sample vessels provided on a sample tray are made of a conductive material and are taken as a common electrode, the necessity of inserting electrodes in the sample vessels as in the conventional apparatus can be eliminated. As a result, since only the capillaries may be inserted in the sample vessels, the preparation for analysis can be facilitated.

By arranging a plurality of the capillaries in parallel and fixing them in position by a capillary retaining plate, the capillaries of the multi-capillary type can be easily inserted in the sample vessels only by moving the sample tray upward using a moving mechanism. As a result, the electrophoresis analysis can be automated using the electrophoresis analysis apparatus of the present invention.

While the specific embodiments have been described using specific terms, such description is for illustrative purposes only, and it is understood that many changes and variations may be made without departing from the spirit or scope of the following claims.

What is claimed:

1. An electrophoresis analysis apparatus comprising:
   a plurality of migration passages;
   a sample tray holder capable of removably fixing a sample tray including a plurality of sample vessels for containing samples;
   a detector for optically detecting sample components separated by electrophoresis;
   a power supply for applying a voltage to the migration passages,
   wherein said sample tray has an electrode capable of contacting the sample in each of said plurality of sample vessels;
   wherein a part of the sample tray holder is electrically connected to the power supply; and
   wherein said part of the sample tray holder is electrically connected to said electrode in response to fixing the sample tray on the sample tray holder.

2. An electrophoresis analysis apparatus according to claim 1, wherein the part of the sample vessel is transparent.

3. An electrophoresis analysis apparatus according to claim 1, wherein the electrode is made of a stainless steel.

4. An electrophoresis analysis apparatus according to claim 1, and further comprising a current detection circuit to monitor a current for each sample.

5. An electrophoresis analysis apparatus according to claim 1, wherein the sample tray comprises a plate portion having a plurality of openings and a metal base portion fixed on a bottom portion of the plate portion.

6. An electrophoresis analysis apparatus according to claim 5, wherein the sample tray further comprises metal pins fixed on the metal base portion, the metal pins having portions projecting in the openings of the plate portion.

7. An electrophoresis analysis apparatus according to claim 1, wherein the sample tray comprises a metal plate portion having a plurality of openings and a base portion fixed on a bottom portion of the plate portion.

8. An electrophoresis analysis apparatus according to claim 1, wherein the sample tray comprises a plate portion having a plurality of openings; a base portion fixed on a bottom portion of the plate portion; and a plate or wire made of conductive material, the plate or wire being in contact with samples.

9. A sample tray capable of being removably fixed on a sample tray holder of an electrophoresis analysis apparatus for separating samples introduced in a plurality of migration passages by electrophoresis, and optically detecting a plurality of sample components, said sample tray having sample vessels for containing samples to be introduced in the migration passages,
   wherein the sample vessels have an electrode capable of contacting each of the samples, which is electrically connected to a part of the sample tray holder upon fixing of the sample tray on the sample tray holder;
   wherein said part of the sample tray holder is electrically connected to a power supply for applying a voltage to the migration passages; and
   wherein the sample tray comprises a plate portion having a plurality of openings and a metal base portion fixed on a bottom portion of the plate portion.

10. A sample tray according to claim 9, wherein the part of the sample vessel is transparent.

11. A sample tray according to claim 9, wherein the electrode is made of stainless steel.

12. A sample tray according to claim 9, wherein the sample tray further comprises metal pins fixed on the metal base portion, the metal pins having portions projecting the openings of the plate portion.

13. A sample tray capable of being removably fixed on a sample tray holder of an electrophoresis analysis apparatus for separating samples introduced in a plurality of migration passages by electrophoresis, and optically detecting a plurality of sample components, said sample tray having sample vessels for containing samples to be introduced in the migration passages,
   wherein the sample vessels have an electrode capable of contacting each of the samples, which is electrically connected to a part of the sample tray holder upon fixing of the sample tray on the sample tray holder;
   wherein said part of the sample tray holder is electrically connected to a power supply for applying a voltage to the migration passages; and wherein the sample tray comprises a metal plate portion having a plurality of openings and a base portion fixed on a bottom portion of the plate portion.

14. A sample tray according to claim 13, wherein the sample tray comprises a plate portion having a plurality of openings; a base portion fixed on a bottom portion of the plate portion; and a plate or wire made of conductive material, the plate or wire being in contact with samples.

* * * * *